United States Patent [19]

Lyons et al.

[11] Patent Number: 5,120,886
[45] Date of Patent: Jun. 9, 1992

[54] DECOMPOSITION OF ORGANIC HYDROPEROXIDES

[75] Inventors: James E. Lyons, Wallingford; Paul E. Ellis, Jr., Downingtown, both of Pa.

[73] Assignee: Sun Refining and Marketing Company, Philadelphia, Pa.

[21] Appl. No.: 727,194

[22] Filed: Jul. 9, 1991

[51] Int. Cl.$^5$ .................. C07C 29/00; C07C 31/12; C07C 33/22; C07C 35/08

[52] U.S. Cl. .................. 568/909.8; 568/807; 568/815; 568/835

[58] Field of Search ............ 568/909.8, 815, 835, 568/807

[56] References Cited

U.S. PATENT DOCUMENTS

| | | | |
|---|---|---|---|
| 4,910,349 | 3/1990 | Sanderson et al. | 568/909.8 |
| 4,912,266 | 3/1990 | Sanderson et al. | 568/909.8 |
| 4,912,267 | 3/1990 | Sanderson et al. | 568/909.8 |
| 4,922,035 | 5/1990 | Sanderson et al. | 568/909.8 |
| 4,922,036 | 5/1990 | Sanderson et al. | 568/909.8 |
| 4,922,602 | 2/1991 | Sanderson et al. | 568/909.8 |
| 4,978,799 | 12/1990 | Sanderson et al. | 568/909.8 |
| 5,004,837 | 4/1991 | Baur et al. | 568/835 |

Primary Examiner—J. E. Evans
Attorney, Agent, or Firm—Q. Todd Dickinson; Donald R. Johnson

[57] ABSTRACT

Hydroperoxides are decomposed by contact with metal ligand catalysts of coordination complexes in which hydrogen in the ligand molecule has been substituted with electron-withdrawing elements or groups, for example halogen or nitro or cyano groups. Preferred catalysts are iron perhaloporphyrins.

8 Claims, 1 Drawing Sheet

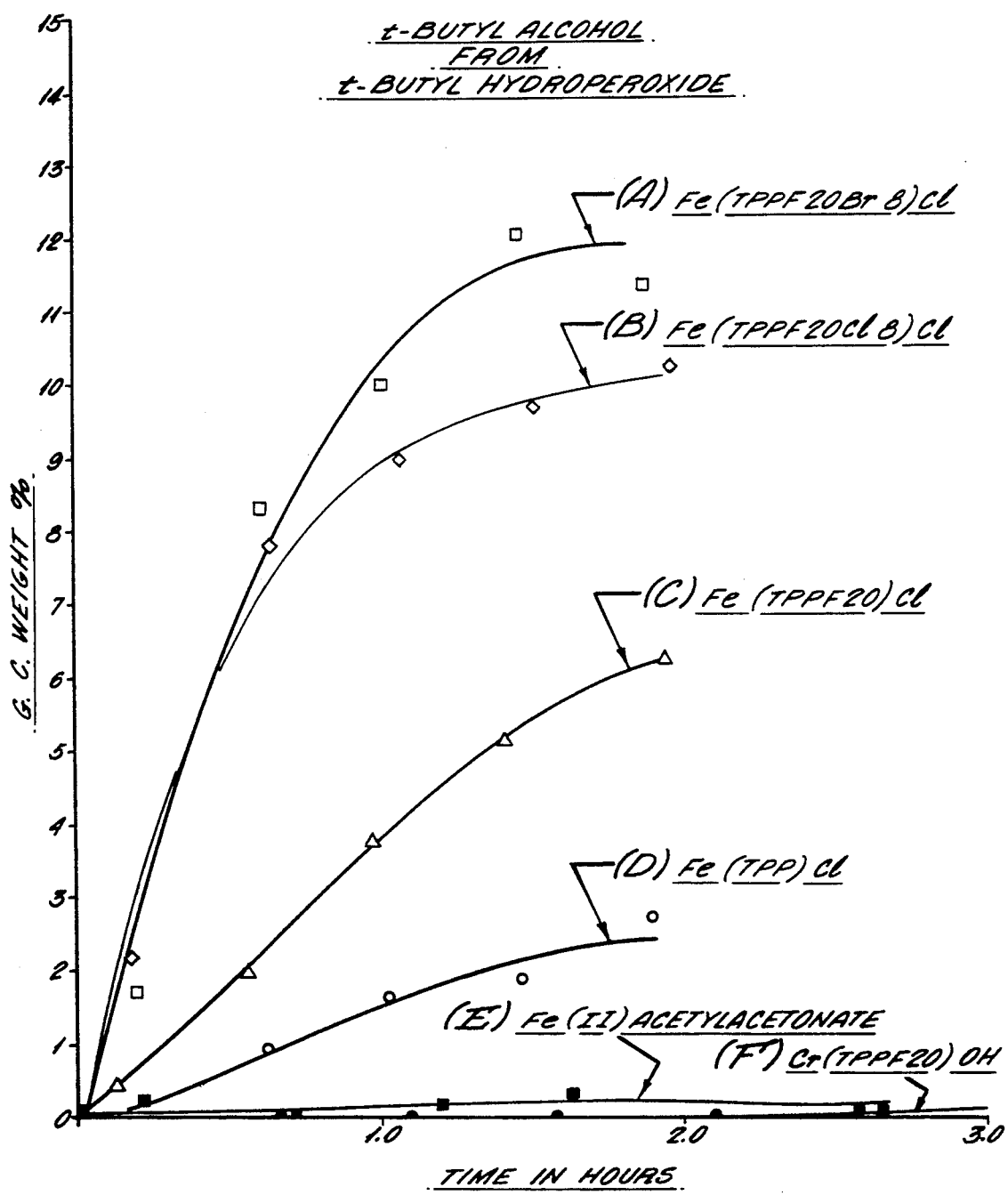

DECOMPOSITION OF ORGANIC HYDROPEROXIDES

BACKGROUND OF THE INVENTION

This invention relates to the decomposition of organic hydroperoxides with metal catalysts which provide desirably high reaction rates, to produce the corresponding alcohol. The catalysts employed according to the invention provide very high reaction rates at relatively low temperatures such as room temperature, in contrast to prior art catalysts which catalyze decomposition of organic hydroperoxides much more slowly and require elevated temperatures in order to achieve satisfactory reaction rates.

DESCRIPTION OF THE PRIOR ART

Taylor et al U.S. Pat. No. 4,551,553 discloses decomposition of hydroperoxide by contact with a catalyst system comprising an admixture of Cr and Ru compounds which are soluble in the liquid hydroperoxide to be decomposed or in a diluent used in the process, such as a hydrocarbon, acid, ester or alcohol diluent, the reaction being conducted at 25° C. to 250° C. and atmospheric to 150 atmospheres pressure, to maintain the reactants in liquid phase. Mixtures of Cr and Ru acetylacetonates are given as examples of the catalysts used. As prior art, Taylor et al disclose catalytic oxidation of hydrocarbons using organic hydroperoxide in the presence of Cr catalyst to produce alcohols and ketones, in U.S. Pat. No. 3,879,467; the decomposition of cycloalkyl hydroperoxides with catalyst comprising a soluble derivative of V, Mo or Ru, in U.S. Pat. No. 3,925,316; decomposition of hydroperoxides with binary homogeneous catalyst combinations of particular salts of Fe and Cu, in U.S. Pat. No. 3,401,193; cyclohexane oxidation and decomposition of resultant cumene hydroperoxide using nonsoluble Re compound, in U.S. Pat. No. 4,173,587; cumene hydroperoxide decomposition studies, employing certain forms of ruthenium, in "Use of the Proton NMR Relaxation Method to Study the Coordination of Cumene Hydroperoxide With Cobalt and Ruthenium Carboxylates" V. M. Nekipelov, Dokl. Akad. Nauk SSSR, V 261 (6), 1377-81 (1981); "NMR Studies of Mu3-Oxo-triruthenium Hexacarboxylate Cumene Hydroperoxide Interaction", A. M. Trzeciak, Oxid. Commun., V. 1(4), p. 295-303 (1980); and "Cumene Hydroperoxide Decomposition Reaction Catalyzed by Ruthenium (III) betadiketonates", A. Trzeciak et al, React. Kinet, Lett., V. 12(1-2), p. 121-5 (1981); and "Decomposition of Organic Hydroperoxides on Ruthenium-pi. - Complexes", Yu A. Aleksandrov, Ah. Obshsch. Khim., V 48, p. 2141 (1978).

Worrell et al U.S. Pat. No. 4,257,852 discloses a distillation process for purifying t-butyl hydroperoxide from an isobutane oxidate mixture. Other components of the oxidate mixture are t-butyl alcohol, water, acetone, organic acids, esters, peroxides.

Sanderson et al U.S. Pat. No. 4,910,349 discloses the preparation of t-butyl alcohol by the catalytic decomposition of t-butyl hydroperoxide, preferably in solution in t-butyl alcohol, in the presence of a metal phthalocyanine of a metal of Group IB, Group VIIB or Group VIIIB, for example chloroferric phthalocyanine and rhenium heptoxide-p-dioxane or oxotrichloro-bis-(triphenylphosphine) rhenium V; at column 7, lines 27 to 35 this patent discloses that iron (III) phthalocyanine is more active than the cobalt (II) phthalocyanine and only 0.05% TBHP remains at 60° C. and 2.0 hours reaction time. At lower temperatures (25° C., 1 hour reaction time), a 5.65% TBHP remains. Under the same conditions but with. an added rhenium complex, the conversion is >99% with no loss in selectivity. Various ratios of Fe to Re and Fe+Re to TBHP were also studied.

Sanderson et al U.S. Pat. No. 4,912,267 discloses a similar preparation to that of U.S. Pat. No. 4,910,349 above, except that a base-promoted metal phthalocyanine catalyst is employed.

Grane et al U.S. Pat. No. 4,296,262 discloses oxidation of isobutane with oxygen-containing gas, using Mo catalyst, and subsequently recovering t-butyl alcohol from the product mixture by distillation.

Sanderson et al U.S. Pat. No. 4,922,035 discloses decomposition of t-butyl hydroperoxide with a metal phthalocyanine (PCY) catalyst, for example chloroferric PCY, promoted with a thiol and a free radical inhibitor.

Sanderson et al U.S. Pat. No. 4,922,036 discloses decomposition of t-butyl hydroperoxide to t-butyl alcohol with a borate-promoted Group IB, VIIB or VIIIB metal PCY such as chloroferric PCY.

Sanderson et al U.S. Pat. No. 4,922,034 discloses decomposition of t-butyl hydroperoxide to t-butyl alcohol using a metal porphine catalyst, for example tetraphenylporphine, optionally promoted with a thiol and a heterocyclic amine.

Sanderson et al U.S. Pat. No. 4,922,033 discloses decomposition of t-butyl hydroperoxide to t-butyl alcohol with a soluble Ru catalyst such as Ru acetylacetonate, promoted with a bidentate ligand such as 2,2'-dipyridyl.

Sanderson et al U.S. Pat. No. 4,912,266 discloses decomposition of t-butyl hydroperoxide with an imidazole-promoted metal PCY catalyst, for example Fe-(III)PCYCl or Mn(II)PCY or VOPCY.

Marquis et al U.S. Pat. No. 4,992,602 discloses a continuous method for converting isobutane to isobutyl alcohol including the step of decomposing t-butyl hydroperoxide to t-butyl alcohol, using a monocyclic aromatic solvent and a PCY decomposition catalyst.

Derwent abstract (Week 8912, Other Aliphatics, page 58) of reference 89-087492/12 (EP 308-101-A) discloses decomposition of t-butyl hydroperoxide to t-butyl alcohol using a metal porphine catalyst such as a trivalent Mn or Fe tetraphenylporphine, optionally promoted with an amine or thiol, or a soluble Ru catalyst promoted with a bidentate ligand such as Ru(acac)3 promoted with bis(salicylidene)ethylenediamine, or a promoted PCY catalyst such as a Mn, Fe or vanadyl PCY promoted with an amine, a Re compound such as NH$_4$ReO$_4$, a mercaptan and a free radical inhibitor, a base or a metal borate.

FURTHER BACKGROUND OF THE INVENTION

The decomposition of hydroperoxides to give the corresponding alcohol has potential commercial importance. Alkyl hydroperoxides are the products of alkane oxidation and their alcohol decomposition products are useful fuel and chemical products. Specifically, t-butyl hydroperoxide is made by the oxidation of isobutane and can be decomposed to the high octane fuel additive, t-butyl alcohol, in the presence of metal complexes. Elevated temperature and/or high catalyst concentration is often needed, and product selectivity is often below 90%.

The process of the invention provides a process for decomposing hydroperoxides to the corresponding alcohol which gives a desired decomposition at a faster rate, allowing lower temperatures and/or lower catalyst concentrations than those required in the prior art and a higher product selectivity at a given reaction temperature. The greater activity of the catalysts of this invention allows them to be used in much lower concentrations resulting in considerable savings in catalyst costs. The process of the invention provides the above and/or other advantages in the decomposition of organic hydroperoxides generally to the corresponding alcohols.

DETAILED DESCRIPTION OF THE INVENTION

The catalyst used according to the invention is a metal coordination complex catalyst containing a transition metal center and a ligand having the structure:

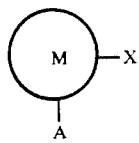

where M is Fe, Mn, Co, Ru or Cr, Fe being preferred, ◯ is a ligand, X is one or more electron-withdrawing substituents for hydrogen in the ligand molecule, for example chloride, bromide, iodide, fluoride, or combinations thereof, or nitro or cyano, or combinations thereof with halogen and A is an anion or is absent. Preferred anions are azide, halide, hydroxide or nitride.

The catalyst used according to one embodiment of the invention is a metal coordination complex catalyst containing a transition metal center and a halogenated ligand, where the ligand is for example tetraphenylporphyrin, related porphyrinato ligands, porphycenes, porphenes, phthalocyanines, 1,3-bis(2-pyridylimino)isoindoline ("BPI") and other 1,3-bis(arylimino)isoindolines, acetylacetonates, acetates, hydroxides, or a Schiff base such as salen, saleph or the like. Preferably the transition metal is iron and the ligand is a perhalogenated porphyrin. Halogenation of the ligand itself, by replacement of hydrogen atoms therein with halogen atoms, and particularly perhalogenation, has been found to increase the activity of these catalysts for the decomposition of hydroperoxides according to the invention by increasing the rate of decomposition to the desired products. The catalyst according to this embodiment of the invention may have, in addition to the halogen atoms in the ligand, an anion, A, namely chloride, fluoride, bromide, iodide, azide, hydroxide or nitride. Preferred among the ligands are such macrocyclic groups as halogenated porphyrins, phthalocyanines, BPI, 1,3-bis(arylamino)isoindolines, Schiff bases and the like. Examples of other ligands which may be employed in the catalysts of this invention are halogenated mono-, bi-, tri, and tetradentate ligand systems such as: propanates, butyrates, benzoates, naphthenates, stearates, acetylacetonates, and other betadiketones, 1,3-bis-(arylimino)-isoindolates, salen, saleph, porphyrinates, porphycenates, porphenates, phthalocyanates, and like systems. Bipyridines, terpyridines, phenanthrolines, dithio-carbamates, xanthates, salicylaldimines, cyclam, dioxy-cyclams, pyrazoylborates, and tetraazamacrocycles such as tetramethyltetraazadibenzocycloheptadecane, may also be used. The halogenated ligands are ligands in which halogen has been substituted for hydrogen in the ligand molecule. The halogens are believed to act as electron-withdrawing agents when the ligand is used as a catalyst for the decomposition of hydroperoxides. Other electron-withdrawing substituents than halogen may also be used, such as nitro or cyano.

The use of cyano- and polycyanometallo porphyrins as catalysts for decomposition of hydroperoxides is contemplated in one embodiment of the invention. Cyano-substituted ligands, like halogen-substituted ligands, are known for their electron withdrawal capabilities. Increased electron withdrawal from halogenation of the porphyrin ring has been correlated to increased catalytic air oxidation activity. J. E. Lyons & P. E. Ellis, Jr., Catalysis Letters, 8, 45 (1991). Cyano groups are known for their large electron-withdrawing inductive effects, and cyano-containing metalloporphyrins with cyano groups in the beta or pyrrolic positions have been shown to be more easily reduced than their precursors without cyano substitution. R. J. Donohoe, M. Atamian and D. F. Bocian, J. Amer. Chem. Soc., 109, 5593 (1987). According to the present invention, such cyano-substituted compounds are used in the catalytic decomposition of hydroperoxides.

The use of nitrated metalloporphyrins as catalysts for decomposition of hydroperoxides is contemplated in another embodiment of the invention. Successive nitration at the meso-positions of Zn(octaethylporphine), eventually giving Zn (meso-tetranitrooctaethyl porphine) has been found to lead to more easily reduced porphyrins, which is evidence for electron withdrawal from the rings. L. C. Gong and D. Dolphin, Can. J. Chem., 63,401–5(1985). Other workers such as Catalano et al in J. Chem. Soc., 1535 (1984) have been able to nitrate the beta or pyrrolic positions in various metal tetraphenylporphyrins. According to the present invention, such nitrated metalloporphyrins are used in catalytic decomposition of hydroperoxides.

The catalysts used according to the invention have been previously disclosed for use in oxidizing alkanes to the corresponding alcohols. Perhalogenated metal complexes have been disclosed in Ellis et al copending application Ser. No. 07/568,118 filed Aug. 16, 1990, the disclosure of which is herein incorporated by reference. Other patents disclosing use of metal coordination complex catalysts in oxidation of alkanes are Ellis et al U.S. Pat. Nos. 4,895,680; 4,895,682 and 4,970,348.

The term "ligand" is used herein in its conventional meaning and refers generically to a group or system of atoms which form one or more bonds to a metal ion, i.e., forms a coordination complex, and stabilizes the coordination complex in desirable oxidation states. Suitable ligands for the present purpose are the well-known phthalocyanines and porphyrins such as alkyl and aryl porphyrins such as tetraphenylporphyrins, octaethylporphyrins, tetramethylporphyrins and the like. Usually there are 0–12 substituents, alkyl or aryl, on the basic porphyrin structure, the alkyls are $C_1-C_4$ and the aryls contain 1 or 2 rings which may themselves have alkyl substituents.

The electron-withdrawing component of the ligand, X, can be fluoride, chloride, bromide, iodide or mixtures thereof, or cyano or nitro, but preferably among the halogens is one of the first three mentioned, more preferably fluoride. The degree of ligand halogenation should be complete, i.e., at least 90%, preferably 100%, which is customarily referred to as perhalogenation for which the conventional symbols are F-, Cl-, etc. We have found that complete halogenation may provide substantially superior results.

The catalysts of our invention can be readily prepared by simple modifications of procedures described in the art for preparing unhalogenated ligands. For example, the unhalogenated Fe(TPP)Cl complex (in which "TPP" is tetraphenylporphyrinato) can be prepared by a standard method in which (TPP)H$_2$ and Fe(II) (or other metal) chloride are refluxed together in a dimethylformamide solution. Purification is achieved by chromatography. (See, e.g., A. D. Adler et al, *J. Inorg. Nucl. Chem.*, 32, 2443 (1970).) From these metal salts the corresponding azides may be prepared by metathesis reactions with dissolved NaN$_3$ or hydrazoic acid.

To prepare the corresponding halogenated ligand coordination complex of this invention, one or more of the precursors of the ligand are halogenated before the ligand itself is produced by a condensation reaction. Thus fluorination of benzaldehyde followed by condensation with pyrrole yields TPPF$_{20}$ in which F$_{20}$ refers to twenty fluorine atoms on the four phenyls. Substituting this TPPF$_{20}$ for TPP in the aforementioned method of refluxing ir a dimethylformamide solution containing the Fe(II) will yield the corresponding Fe(TPPF$_{20}$) salt.

By way of specific illustration the perhalogenated metal porphyrin, [Fe(TPPF$_{20}$Br$_8$)]Cl, iron tetrakispentafluorophenyloctabromoporphyrin) chloride, is prepared as follows: Under N$_2$, a flask is charged with 1.0 g of Zn(TPPF$_{20}$) and 300 ml of CCl$_4$. This mixture is refluxed with 150 ml of 6M Br$_2$ for 5 hours and is then allowed to cool to room temperature. After chromatography on basic alumina, 300 mg. of pure Zn(TPPF$_{20}$Br$_8$) is obtained and characterized by UV/VIS, IR and elemental analysis. The zinc is removed by acid treatment and the iron complex Fe(TPPF$_{20}$Br$_8$)Cl, is prepared by FeCl$_2$ treatment in refluxing DMF. The azide, Fe(TPPF$_{20}$Br$_8$)N$_3$, can be prepared by reaction of the chloride salt with NaN$_3$ in acetone. The ruthenium, chromium and manganese complexes are prepared similarly. The hydroxo salt, Fe(TPPF$_{20}$Br$_8$)OH, is prepared from the chloro salt by treatment with dilute aqueous KOH in CH$_2$Cl$_2$/H$_2$O.

The perhalogenated metal porphyrin Fe(TPPF$_{20}$Cl$_8$)Cl is prepared as follows: under N$_2$, 0.5 g of Zn(TPPF$_{20}$) dissolved in 500 ml of CCl$_4$ is refluxed for 5 hr. while Cl$_2$ gas is bubbled slowly through the solution. After cooling the mixture is filtered and chromatographed on alumina, yielding 0.4 g of pure Zn(TPPF$_{20}$Cl$_8$)Cl$_8$. The zinc is removed by trifluoroacetic acid treatment, and the iron is then inserted by reaction with FeCl$_2$ in DMF. The resulting Fe(TPPF$_{20}$Cl$_8$)Cl is characterized by UV/VIS, IR, and elemental analysis. The ruthenium, manganese, and chromium complexes are prepared similarly. The azide salts are prepared from the chloride salts by metathesis with NaN$_3$ in acetone. The hydroxo salt, Fe(TPPF$_{20}$Cl$_8$)OH, is prepared from the chloro salt by treatment with dilute aqueous KOH solution in CH$_2$Cl$_2$.

The perfluorinated metal porphyrin, iron perfluorotetraphenylporphyrin chloride, Fe(TPPF$_{28}$)Cl (28 F atoms) can be prepared by the reaction of dilute F$_2$ gas in N$_2$ with Zn(TPPF$_{20}$) in CCl$_4$, with small added amounts of CoF$_3$, followed by removal of zinc and incorporation of iron as before. This porphyrin complex is analyzed by IR, UV/VIS, and elemental analysis. The ruthenium, chromium, and manganese complexes are prepared in analagous fashion. The azide salts are prepared from the chloride salts by reaction with NaN$_3$ in acetone. The hydroxo salt, Fe(TPPF$_{28}$)OH, is prepared by the dilute aqueous KOH treatment of the chloro salt in CH$_2$Cl$_2$.

The preparation of the following iron complexes are examples of the tetraalkylporphyrins used in our invention. Freshly distilled pyrrole (0.8 g) and trifluoroacetaldehyde methyl hemiacetal (10.9 g) are refluxed for 24 hr. in 500 ml of ethanol containing 10 ml of 48% HBr. After neutralization of the mixture and extraction of the crude tetrakis(trifluoromethyl) porphyrin into CH$_2$Cl$_2$, the H$_2$(TTFMP) is purified by chromatography with alumina. Iron is inserted into the H$_2$(TTFMP) by FeCl$_2$/DMF treatment giving Fe(TTFMP)Cl. The azide and hydroxide complexes are prepared by metathesis with NaN$_3$ in acetone and aqueous KOH in CH$_2$Cl$_2$, respectively. The pyrrolic hydrogens of this porphyrin can be partially or fully halogenated with Br, Cl, or F using the same techniques used for the tetraphenylporphyrins. As an example, dilute F$_2$ gas treatment of Zn(TTFMP) in the presence of CoF$_3$ in CCl$_4$ leads to isolation of the perfluorinated zinc porphyrin, zinc perfluorotetramethylporphyrin Zn(FTMP). Removal of the zinc by strong acid treatment leads to the metal free H$_2$(FTMP) from which the iron complex Fe(FTMP)Cl can be prepared by FeCl$_2$/DMF treatment. The azide, hydroxide, and nitride complexes are prepared in similar fashion to those described before. The chromium, manganese, and ruthenium complexes can be prepared from H$_2$-FTMP by use of the appropriate metal chloride or metal acetate in DMF.

Other metal halogenated porphyrins or phthalocyanines are made analogously to the above methods. Similarly, when other porphyrin compounds are used similar results are obtained. The excellent catalytic activity of our catalyst depends on the electronic and structural nature of the porphyrin and phthalocyanine macro structure itself, not on any specific substituted group.

From the foregoing it will be seen that the catalysts used in the process of the invention are comprised of the component parts: the ligand moiety, which has been substituted with electron-withdrawing elements or groups, for example having been halogenated or substituted with cyano or nitro groups, the metal center which is bound to (i.e., complexed with) the ligand, and as anion, azide, chloride, hydroxide or nitride or the like, which is bound to the metal. The metal-ligand portion is also frequently described in the art as a metal coordination complex. In some cases, dimetal $\mu$-oxo compounds, commonly known as $\mu$-oxo dimers, are suitable catalysts and should be regarded as the equivalent thereof. In these compounds, each of the two iron centers is bound to one anion moiety. A typical structure for such compounds is:

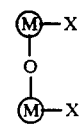

where M and X are as previously defined. This compound may also be characterized by the structure:

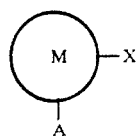

where M and X are as previously defined and A is:

The catalyst use the process according to the invention may also be prepared by the method disclosed and claimed in Ellis et al U.S. patent application Ser. No. 07/634,261 filed Dec. 7, 1990, the disclosure of which is herein incorporated by reference. As a typical reaction according to that application, the perhalogenation is performed by reaction of iron tetrakispentafluorophenyl)-porphyrinato with bromine.

Nitro-substituted porphyrins are prepared for example by reacting iron tetrakispentafluorophenyl chloride with 1 to 8 equivalents of nitrogen dioxide in methylene dichloride or benzene, leading to various amounts of nitration at the beta positions on the ring according to the severity of the reaction conditions. Beta positions left unnitrated are subsequently halogenated using normal chlorination, bromination or fluorination techniques. The general structure for this preparation is:

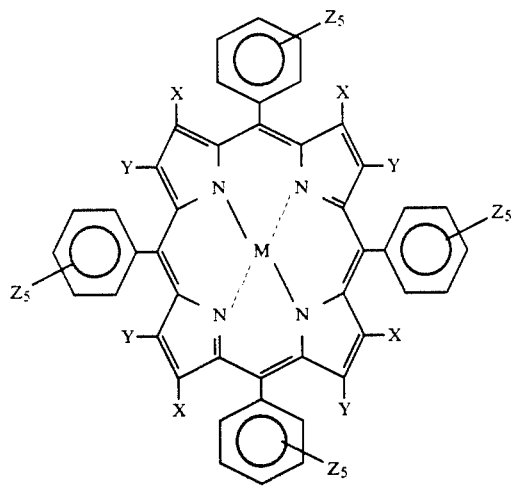

where M is Fe, Cr, Mn, Ru, Co, or Cu, X is $NO_2$, Y is $NO_2$, Cl, Br or F and Z is H, Cl or F.

Alternatively, Zn(porphine) is reacted with nitrogen dioxide in methylene chloride to produce Zn (mesotetranitroporphine). The zinc is removed by acid treatment and Fe or other transition metal, M, is inserted by the usual method of ferrous chloride or metal dichloride in dimethylformamide. The beta or pyrrolic hydrogens can be further nitrated or halogenated as desired. The general structure for this preparation is:

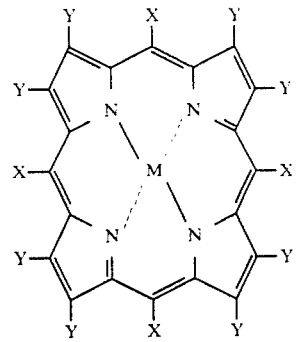

where M is Fe, Cr, Mn, Ru, Cu or Co, X is $NO_2$, Y is $NO_2$, Cl, F, Br, or any combination thereof.

Meso-perfluorinated alkyl porphyrins as disclosed in our copending application Ser. No. 568,118 filed Aug. 16, 1990, the disclosure of which is incorporated by reference herein, can be nitrated in the beta or pyrrolic positions using nitrogen dioxide in methylene chloride or nitric/sulfuric nitrating solutions. The general structure for this preparation is:

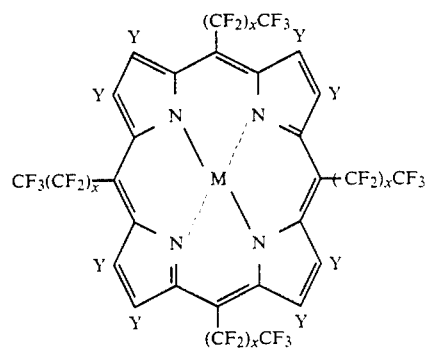

where M is Fe, Cr, Mn, Ru, Cu or Co, X is 0 to 6, and Y is $NO_2$ and Cl, Br or F.

Cyano-substituted porphyrins are prepared for example by bromination of Zn(tetrakispentafluoroporphine) with bromine in carbon tetrachloride to obtain Zn(tetrakispentafluorophenyl-beta-octabromoporphine), which is then treated with 9 equivalents of CuCN in pyridine at reflux for several hours. After chromatography several of the bromines are replaced with CN groups giving, according to the conditions, $Zn(TPPF_{20}\text{-beta-}CN_{4-8})$. The zinc is removed by mild treatment with 1M HCl and recovered by chromatography on alumina. Metals can be inserted into the product, $H_2(TPPF_{20}\text{-beta-}CN_{4-8})$ by treatment with the metal salt in DMF, e.g., ferrous chloride in DMF, leading to the production of $Fe(TPPF_{20}\text{beta-}CN_{4-8})Cl$.

If the CuCN treatment is conducted under milder conditions some of the bromine groups can be reatined leading to mixed bromo/dyano metalloporphyrins. Pyrrolic positions without cyano or bromo substitution can also be brominated, chlorinated or fluorinated leading to complexes of the general structure;

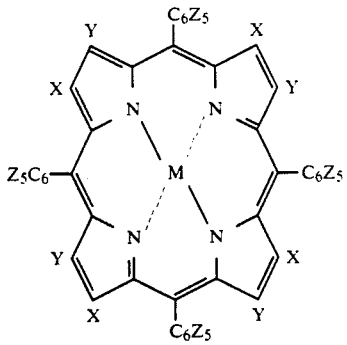

where M is Fe, Cr, Mn, Ru, Co or Cu, X is CN, Y is CN, Cl, Br or F and Z is H, Cl or F.

Meso-perfluorinated alkyl porphyrins can also be converted to cyano derivatives as shown in the previous examples. The general structure is:

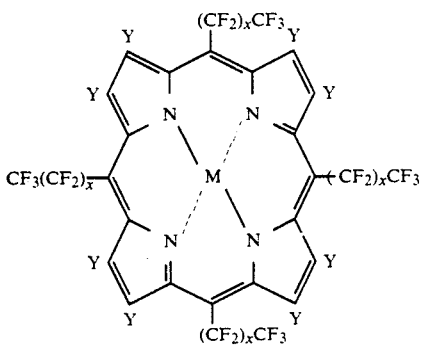

where M is Fe, Cr, Mn, Ru, Cu or Co, X is 0 to 6, and Y is CN and Cl, Br or F.

The decomposition of hydroperoxide according to the invention is preferably carried out in a solution of the hydroperoxide, preferably a solution containing from about 5 to about 50 wt. % of hydroperoxide. Suitable solvents include benzene, chlorobenzene, o-dichlorobenzene, acetonitrile, benzonitrile, alcohols, ketones and the like. A useful solvent is the alcohol which is formed by decomposition of the hydroperoxide, for example, t-butanol formed by decomposition of t-butylhydroperoxide. A suitable solvent can be selected by a person skilled in the art. Any suitable temperature and pressure may be used. Preferably the temperature is in the range from 25° to 100° C. The time of reaction may be relatively short, in view of the rapid reaction rate with the catalysts employed according to the invention, but will typically be in the range from 0.1 to 5 hours.

In the process of the invention, the hydroperoxide dissolved in a solvent is introduced into a reaction zone wherein it is contacted with catalyst, in the substantial absence of added oxidizing agent, to convert the hydroperoxide, ROOH, where R is an organic radical, to the corresponding alcohol, ROH.

Hydroperoxides which may be decomposed according to the invention include compounds having the formula ROOH, where R is an organic radical, typically a straight or branched chain alkyl or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to about 15 carbon atoms and a halogen atom such as chloride, bromide, or an alkaryl group in which the alkyl chain contains from 1 to 15 carbon atoms and the aryl group is as above described. Preferably, R is an alkyl or cycloalkyl group containing 4 to 12 carbon atoms or an alkaryl group in which the aromatic moiety is phenyl and the alkyl substitutent is straight or branched chain alkyl or cycloalkyl containing up to about 6 carbon atoms. Examples are t-butyl and isobutyl hydroproxide, isoaml hydroperoxide, 2-methylbutyl-2-hydroperoxide, cyclohexyl hydroperoxide, alpha- and beta-ethylbenzene hydroperoxide, cumyl hydroperoxide, phenethyl hydroperoxide and cyclohexylphenyl hydroperoxide. Phenethyl hydroperoxide and cumyl hydroperoxide are each converted to phenethyl alcohol.

The invention will be further described below in connection with Example 2, with reference to the drawing, in which FIG. 1 is a plot of t-butyl alcohol produced in examples according to the invention and comparison examples, against reaction time.

The following examples illustrate the invention:

EXAMPLE 1

Tertiary butyl hydroperoxide (90%), 10 ml. was added dropwise over a 6-13 minute period to a stirred solution of $2 \times 10^{-4}$ mmole of the catalyst complex in 50 ml of benzene. Aliquots (ml) were withdrawn at 25 min. intervals and analyzed by glpc. The complex was an iron porphyrin complex as shown in Table I. The results for four different complexes were as shown in Table I. The first and second complexes were perhalogenated complexes, the third a partially halogenated complex and the fourth contained an unhalogenated triphenylporphyrin complex.

TABLE I

| t-BUTYLHYDROPEROXIDE DECOMPOSITION CATALYZED BY IRON PORPHYRIN COMPLEXES AS A FUNCTION OF THE EXTENT OF PORPHYRIN RING HALOGENATION | | | | | |
|---|---|---|---|---|---|
| | Reaction Time. Hrs. | Reaction Products, | | mmoles $(tBuO)_2$ | tBu$_2$OH Conv. % | tBuOH Sel. % |
| | | tBuOH | Acetone | | | |
| Fe(TPPF$_{20}\beta$-Br$_8$)Cl | 1.9 | 91.3 | 2.1 | 4.2 | 99 | 94 |
| Fe(TPPF$_{20}\beta$-Cl$_8$)Cl | 1.9 | 89.0 | 2.1 | 3.9 | 98 | 94 |
| Fe(TPPF$_{20}$)Cl | 2.0 | 44.2 | 2.9 | na | 62 | <94 |
| Fe(TPP)Cl | 1.9 | 19.1 | 3.3 | na | 29 | <85 |

EXAMPLE 2

Further data on the process of the invention are shown in FIG. 1, which is a plot of weight percent t-butyl alcohol formed against reaction time in the reactions carried out a described in Example 1, using different complexes in each of six runs. Complexes A and B as shown in FIG. 1 were perhalogenated iron porphyrin complexes, complex C a partially halogenated complex, complex D contained an unhalogenated porphyrin complex, complex E was Fe(II)acetylacetonate and complex F was Cr(TPPF)OH where TPPF is perfluorinated porphyrin.

EXAMPLE 3

Table II shows in Runs 1-6 and 11, the results after one hour reaction time for the seven catalysts shown in FIG. 1. Table II also shows the results after one hour reaction time for the other catalysts identified in Table II. The reactions were carried out in the same manner as described in Example 1. In Table II, "AA" is acetylacetonate, "PcF" is perfluorophthalocyanine, "$N_3$" is azide, "BPI" is 1,3-bis-(2-pyridylimino)isoindoline, "OAc" is acetate, "OO-t-$C_4$" is tertiarybutyl-peroxy, "Pc" is phthalocyanine, "$F_3AAF_3$ is perfluoroacetylacetonate. The values given for "Wt. % $C_4$OH" include 0.6 (plus or minus 0.2) wt. % $C_4$OH(t-butyl alcohol) in the starting material.

TABLE II

| | CATALYTIC HYDROPEROXIDE DECOMPOSITION | | | |
|---|---|---|---|---|
| RUN | CATALYST .0033 mM./L. | t-$C_4H_9$OH G.C.Wt. % | t-$C_4H_9$OOH G.C.Wt. % | $(CH_3)_2CO$ G.C.Wt. % |
| 1 | Fe(III) [TPPF$_{20}$]Br$_8$Cl | 11.2 | 2.3 | 0.2 |
| 2 | Fe(III) [TPPF$_{20}$Cl$_8$]Cl | 9.8 | 2.9 | 0.3 |
| 3 | Fe(III) [TPPF$_{20}$]Cl | 4.7 | 9.7 | 0.4 |
| 4 | Fe(III)[TPPF$_{20}$]Cl | 6.6 | 11.9 | 0.1 |
| 5 | Fe(III) [TPP]Cl | 2.3 | 13.2 | 0.4 |
| 6 | Fe(II) [AA]$_2$ | 1.0 | 15.0 | 0.4 |
| 7 | Fe(III) [PcF]N$_3$ | 0.8 | 15.0 | 0.2 |
| 8 | Fe(II) [PcF] | 0.9 | 15.5 | 0.2 |
| 9 | Co(II) [PBI] [OAc] [OO-t-C$_4$] | 0.6 | 15.9 | 0.2 |
| 10 | Fe(III) [AA]$_3$ | 0.5 | 15.9 | 0.2 |
| 11 | Cr(III) [TPPF$_{20}$]OH | 1.0 | 16.0 | 0.3 |
| 12 | Co(II) [TPPF$_{20}$]Cl$_8$ | 0.7 | 16.0 | 0.2 |
| 13 | Mn(III) [TPPF$_{20}$]N$_3$ | 0.6 | 16.0 | 0.2 |
| 14 | Fe(II) [Pc] | 0.6 | 16.0 | 0.2 |
| 15 | Fe(III) [F$_3$AAF$_3$]$_3$ | 0.5 | 16.0 | 0.2 |
| 16 | Co(II) [TPP] | 0.4 | 16.0 | 0.2 |

Runs 1, 2, 3, 4, 7, 8, 11, 12, 13 and 17 in Table II were performed with catalysts according to the invention. The best results were obtained with catalysts containing Fe and porphyrin (Runs 1-4). Runs with Fe and halogenated phathalocyanine (Runs 7 and 8), Cr and halogenated porphyrin (Run 11), Co and halogenated porphyrin (Run 12), Mn and halogenated porphyrin (Run 13), Fe and halogenated acetylacetonate (Run 15) gave poore results. Satisfactory reaction rates for the catalysts of Runs 7, 8, 11, 12, 13 and 15 may be obtained by using higher catalyst concentrations and/or by raising the temperature; however, raising the temperature may result in loss of selectivity, and the results obtained with the halogenated ligands of Runs 7, 8, 11, 12, 13 and 15 may not be improved over the corresponding unhalogenated ligand. In any event, the ligands of Runs 1-4 are clearly much superior to those of Runs 7, 8, 11, 12, 13 and 15.

What is claimed is:

1. Process for the decomposition of a hydroperoxide which comprises contacting the hydroperoxide with a catalyst having the formula

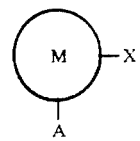

where M is Fe, Mn, Co, Cu, Ru, or Cr, ◯ is a ligand, X is one or more electron-withdrawing substituents for hydrogen in the ligan molecule selected from the group consisting of halogen, cyano, and nitro groups or combinations thereof, and A is an anion or is absent, and where, if X is halogen, the degree of ligand halogenation is at least 90%.

2. Process according to claim 1 wherein the metal is iron.

3. Process according to claim 1 wherein ◯ is a porphyrin.

4. Process according to claim 1 wherein X is fluoride.

5. Process according to claim 1 wherein X is a combination of fluoride and bromide.

6. Process according to claim 1 wherein said catalyst is iron(tetrakispentafluorophenyloctabromoporphyrin)-chloride.

7. Process according to claim 1 wherein said catalyst is iron(tetrakispentafluorooctachloroporphyrin)chloride.

8. Process according to claim 1 wherein said catalyst is iron perfluorotetraphenylporphyrin chloride.

* * * * *